United States Patent
Ripley et al.

(10) Patent No.: US 9,445,564 B1
(45) Date of Patent: Sep. 20, 2016

(54) CANOLA INBRED LINE DN051465A

(71) Applicant: Agrigenetics, Inc., Indianapolis, IN (US)

(72) Inventors: Van L. Ripley, Grandora (CA); Michelle E. Beaith, Saskatoon (CA)

(73) Assignee: Agrigenetics, Inc., Indianapolis, IN (US)

( * ) Notice: Subject to any disclaimer, the term of this patent is extended or adjusted under 35 U.S.C. 154(b) by 49 days.

(21) Appl. No.: 14/090,197

(22) Filed: Nov. 26, 2013

Related U.S. Application Data

(60) Provisional application No. 61/731,125, filed on Nov. 29, 2012.

(51) Int. Cl.
*A01H 5/10* (2006.01)

(52) U.S. Cl.
CPC ................................. *A01H 5/10* (2013.01)

(58) Field of Classification Search
None
See application file for complete search history.

(56) References Cited

U.S. PATENT DOCUMENTS

| | | |
|---|---|---|
| 5,523,520 A | 6/1996 | Hunsperger et al. |
| 5,850,026 A | 12/1998 | DeBonte et al. |
| 5,912,421 A | 6/1999 | Boerboom |
| 5,959,185 A | 9/1999 | Streit |
| 5,973,234 A | 10/1999 | Mueller |
| 5,977,445 A | 11/1999 | Soper |
| 6,025,547 A | 2/2000 | Stucker |
| 6,096,953 A | 8/2000 | Hoffbeck |
| 6,248,876 B1 | 6/2001 | Barry |
| 6,355,867 B1 | 3/2002 | Bradbury |
| 6,433,254 B1 | 8/2002 | Sernyk |
| 6,444,879 B1 | 9/2002 | Sernyk |
| 6,455,763 B1 | 9/2002 | Sernyk |
| 6,489,543 B1 | 12/2002 | Sernyk |
| 6,815,594 B2 | 11/2004 | Dragonuk et al. |
| 6,906,251 B1 | 6/2005 | Morrow |
| 7,348,473 B2 | 3/2008 | Kubik |
| 7,351,882 B2 | 4/2008 | Patel |
| 7,355,100 B2 | 4/2008 | Kubik |
| 7,408,099 B1 | 8/2008 | Tietz |
| 7,411,117 B2 | 8/2008 | Bohning |
| 7,456,339 B2 | 11/2008 | Patel |
| 7,723,581 B2 * | 5/2010 | Chungu .............. A01H 5/10 435/430 |
| 7,820,889 B1 | 10/2010 | Byrnes et al. |
| 2003/0005479 A1 | 1/2003 | Kato |
| 2004/0025207 A1 | 2/2004 | Garing |
| 2006/0075516 A1 | 4/2006 | Kubik |
| 2006/0075517 A1 | 4/2006 | Kubik |
| 2006/0225146 A1 | 10/2006 | Kubik |
| 2006/0225159 A1 | 10/2006 | Kubik |
| 2006/0265778 A1 | 11/2006 | Veldboom |
| 2008/0256653 A1 | 10/2008 | Chungu |
| 2008/0256655 A1 | 10/2008 | Chungu |
| 2008/0256656 A1 | 10/2008 | Chungu |
| 2008/0260930 A1 | 10/2008 | Chungu |
| 2008/0263715 A1 | 10/2008 | Chungu |
| 2008/0263717 A1 | 10/2008 | Chungu |
| 2009/0276914 A1 | 11/2009 | Stangland |
| 2011/0191880 A1 | 8/2011 | Kubik |
| 2011/0191881 A1 | 8/2011 | Kubik |
| 2011/0191882 A1 | 8/2011 | Kubik |
| 2011/0191883 A1 | 8/2011 | Kubik |
| 2011/0191884 A1 | 8/2011 | Chungu |
| 2011/0191885 A1 | 8/2011 | Kubik |
| 2011/0191886 A1 | 8/2011 | Chungu |
| 2011/0191888 A1 | 8/2011 | Chungu |
| 2011/0191889 A1 | 8/2011 | Chungu |
| 2012/0174250 A1 | 7/2012 | Ripley |
| 2012/0174251 A1 | 7/2012 | Kubik |
| 2012/0174252 A1 | 7/2012 | Kubik |
| 2012/0174266 A1 | 7/2012 | Kubik |
| 2012/0216310 A1 | 8/2012 | Kubik |
| 2012/0216311 A1 | 8/2012 | Kubik |

FOREIGN PATENT DOCUMENTS

| | | |
|---|---|---|
| EP | 0242246 | 10/1987 |
| EP | 0333033 | 9/1989 |
| WO | WO9302197 | 2/1993 |
| WO | WO9319181 | 9/1993 |
| WO | WO9400992 | 1/1994 |
| WO | WO9516776 | 6/1995 |
| WO | WO9518855 | 7/1995 |
| WO | WO9630517 | 10/1996 |
| WO | WO 9630530 | 10/1996 |
| WO | WO2005012515 | 2/2005 |
| WO | WO2005107437 | 11/2005 |
| WO | WO2007016521 | 2/2007 |

OTHER PUBLICATIONS

Allard, In Principles of Plant Breeding, John Wiley & Sons, Inc. pp. 155-156, 1960.
Phillips, et al., "Cell/Tissue Culture and in Vitro Manipulation," In Corn and Corn Improvement, ASA Monograph No. 18, 3rd edition, pp. 345, 358, 1988.
Eshed, et al., "less-than-additive epistatic interactions of quantitative trait loci in tomato," Genetics (1996), vol. 143, pp. 1807-1817.
Kraft, et al., "Linkage disequilibrium and fingerprinting in sugar beet," Theoretical Applied Genetics (2000), vol. 101, pp. 323-326.
Murray, et al., Proceedings of the 43rd Annual Corn and Sorghum Industry Research Conference, vol. 43, p. 72-87, 1988.
Nesi, et al., "Genetic and molecular approaches to improve nutritional value of *Brassica napus* L. seed" Science Direct, C.R. Biologies 331 (2008) 763-771.

* cited by examiner

*Primary Examiner* — Elizabeth McElwain
(74) *Attorney, Agent, or Firm* — Marcia I. Rosenfeld

(57) ABSTRACT

The present invention relates to a new and distinctive canola, designated DN051465A. Also included are seeds of canola DN051465A, to the plants, or plant parts, of canola DN051465A and to methods for producing a canola plant produced by crossing the canola DN051465A with itself or another canola genotype, and the creation of variants by mutagenesis or transformation of canola DN051465A.

20 Claims, No Drawings

CANOLA INBRED LINE DN051465A

CROSS-REFERENCE TO RELATED APPLICATIONS

This Application claims the benefit of U.S. Provisional Application 61/731,125 filed on Nov. 29, 2012.

FIELD OF THE INVENTION

This invention relates to a canola inbred line designated DN051465A that includes plants, DNA, and seeds of canola DN051465A. Methods for producing canola plants, such as canola plant varieties, hybrid canola plants, or other canola plants, as by crossing canola DN051465A with itself or any different canola plant are an integral part of this invention as are the resultant canola plants including the plant parts and seeds. This invention further relates to methods for producing DN051465A-derived canola plants, to methods for producing male sterile DN051465A canola plants, e.g., cytoplasmic male sterile DN051465A canola plants, and to methods for regenerating such plants from tissue cultures of regenerable cells as well as the plants obtained there from. Methods for producing a canola plant from DN051465A containing in its genetic material one or more transgenes and to the transgenic canola plants produced by that method are also part of this invention.

BACKGROUND OF THE INVENTION

"Canola", refers to a particular class of rapeseed (*Brassica napus oleifera annua*) having: (i) a seed oil that contains less than 2% erucic acid, and (ii) an oil-free meal that contains less than 30 micromoles aliphatic glucosinolates per gram of meal. Canola seed is pressed for cooking oil and the residual meal is used as an organic fertilizer and as a high-protein animal feed supplement. Industrial uses of canola include biodiesel and plastic feedstocks.

Farmers in Canada began producing canola oil in 1968. Early canola cultivars were known as single zero cultivars because their oil contained 5% or less erucic acid, but glucosinolates were high. In 1974, the first licensed double zero cultivars (low erucic acid and low glucosinolates) were grown. Today all canola cultivars are double zero cultivars. The Canadian Health and Welfare Department recommended conversion to the production of low erucic acid varieties of rapeseed. Industry responded with a voluntary agreement to limit erucic acid content to less than 5% in food products, effective Dec. 1, 1973. In 1985, the U.S. Food and Drug Administration granted canola oil GRAS (Generally Recognized as Safe) status for use in human foods.

Because canola oil is perceived to be "healthy", its use is rising steadily both as an oil for cooking and as an ingredient in processed foods. The consumption of canola oil is expected to surpass corn and cottonseed oils, becoming second only to soybean oil. It is low in saturated fatty acids and high in monounsaturated fatty acids, containing a high level of oleic acid. Many people prefer the light color and mild taste of canola oil over olive oil, the other readily available oil high in monounsaturates.

Canola is an important and valuable field crop. The goal of a canola breeder is to develop new, unique, and superior canola cultivars and hybrids having improved combinations of desirable traits and therefore, increased economic value. Improved performance is manifested in many ways. Higher yields of canola plants contribute to higher seed production per acre, a more profitable agriculture and a lower cost of products for the consumer. Improved plant health increases the yield and quality of the plant and reduces the need for application of protective chemicals. Adapting canola plants to a wider range of production areas achieves improved yield and vegetative growth. Improved plant uniformity enhances the farmer's ability to mechanically harvest canola. Improved nutritional quality increases its value in food and feed.

Canola is a dicot plant with perfect flowers, i.e., canola has male, pollen-producing organs and separate female, pollen receiving organs on the same flower. Canola flowers are radial with four sepals alternating with four petals forming the typical cross pattern from which the Cruciferae family derives its name. In addition, canola flowers consist of two short lateral stamens, four longer median stamens and a stigma. Pollination occurs with the opening of the anthers and shedding of pollen on the stigma or with the deposit of pollen on the stigma by insects. Canola flowers are mainly self-pollinating, although outcrossing occurs when pollen is transferred from the anthers to the stigmas by wind or bees or other insects. After fertilization, which is usually complete within 24 hours of pollination, the syncarpous ovary elongates to form a silique (pod). Because each pod may contain 25 or more seeds and each plant produces many pods, the multiplication rate per generation usually exceeds 1,000 to 1, thereby accelerating the breeding and evaluation process.

The development of new cultivars in a canola plant breeding program involves numerous steps, including: (1) selection of parent canola plants (germplasm) for the initial breeding crosses; (2) producing and selecting inbred breeding lines and cultivars by either the doubled-haploid method or repeated generations of selfing individual plants, which eventually breed true; (3) producing and selecting hybrid cultivars by crossing a selected inbred male-sterile line with an unrelated inbred restorer line to produce the $F_1$ hybrid progeny having restored vigor; and (4) thoroughly testing these advanced inbreds and hybrids compared to appropriate standards for three or more years in environments representative of the commercial target area(s). The best inbred and hybrid experimental cultivars then become candidates for new commercial cultivars. Those lines still deficient in a few traits may be used as parental lines to produce new populations for further selection.

Development and selection of new canola parental lines, the crossing of these parental lines, and selection of superior hybrid progeny are vital to maintaining a canola breeding program. The $F_1$-hybrid canola seed is produced by manual crosses between selected male-fertile parents or by using male-sterility systems. These hybrids are selected for certain single-gene traits such as pod color, flower color, pubescence color or herbicide resistance, which can indicate that the seed is truly a hybrid from the intended cross. Additional data on parental lines, as well as the phenotype of the hybrid, influence the breeder's decision whether to continue with the specific hybrid cross.

The method of doubled-haploid breeding consists of donor selection, microspore culture and chromosome doubling, embryo cold stress, plantlet regeneration, ploidy analysis, and self-pollination to produce seed of doubled-haploid lines. The advantage of the doubled-haploid method is that the time to develop a new completely homozygous and homogeneous cultivar can be reduced by 3 years compared to the conventional inbreeding method of multiple generations of self pollination.

When two different, unrelated canola parent cultivars are crossed to produce an $F_1$ hybrid, one parent cultivar is designated as the male, or pollen parent, and the other parent cultivar is designated as the female, or seed parent. Because canola plants are capable of self-pollination, hybrid seed production requires elimination of or inactivation of pollen produced by the female parent. Different options exist for controlling male fertility in canola plants such as physical emasculation, application of gametocides, and cytoplasmic male sterility (CMS).

Hybrid canola seed can be produced on a commercial scale by means of a system whereby the female parent has an allele in the mitochondrial genome for cytoplasmic male sterility and the male parent has an allele in the nuclear genome for fertility restoration (Rf). Cytoplasmic male sterility prevents the production of functional pollen, thereby preventing self pollination of the female parent. Pollen from the male parent planted in close proximity to the female parent is then able to freely cross pollinate the female parent to produce hybrid seed. The fertility-restoration allele contributed by the male parent to the seed embryo enables the hybrid crop plants to be male fertile. The resulting hybrid canola crop, which is fully fertile, may then demonstrate heterosis (increased vigor) to produce grain yields potentially greater than that of inbred cultivars.

A cytoplasmic male-sterile inbred (A) line is genetically maintained and increased in a breeding and hybrid-production program by growing it in isolation with a male-fertile maintainer (B) line that is normal (N) for cytoplasmic fertility and is homozygous recessive at the nuclear male-fertility restoration locus (rfrf). All seed harvested from the A line is then male sterile (S rfrf) and all seed harvested off the B line is male fertile (N rfrf). The A line is then maintained, increased, and used as the female parent for hybrid seed production in combination with an unrelated male parent that has the dominant allele (Rf) for male fertility restoration.

One example of a CMS system in canola hybrid production and breeding is the Ogura (Ogu) cytoplasm and its specific nuclear fertility-restoration gene, Rfo—a system discovered in radish (*Raphanus sativus*) and transferred to *Brassica napus* after protoplast fusion. The system was later improved by breeding to lower the glucosinolate content for hybrid canola.

These processes, which lead to the final step of marketing and distribution of a cultivar, usually take from 8 to 12 years from the time the parental cross is made. Therefore, development of new canola inbred and hybrid cultivars is a slow, costly process that requires the resources and expertise of plant breeders and numerous other specialists.

It is nearly impossible for two canola breeders to independently develop genetically-identical canola inbreds or hybrids expressing all the same trait characteristics. The cultivars that are developed cannot be predicted because the breeder's selection occurs in unique environments, with no control over meiotic genetic recombination (using conventional breeding procedures), and with millions of different possible genetic combinations possible. A breeder of ordinary skill in the art cannot predict the final resulting lines he/she develops, except possibly in a very gross and general fashion. The same breeder cannot produce the same cultivar twice by using the exact same original parents and the same selection techniques.

Canola cultivars and other sources of canola germplasm are the foundation material for all canola breeding programs. Despite the existence and availability of numerous canola cultivars and other source germplasm, a need still exists for the development of improved germplasm to improve and maximize yield and quality.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods that are meant to be exemplary and illustrative, not limiting in scope.

According to the invention, there is provided a novel canola inbred line designated DN051465A. This invention thus relates to the seeds of canola DN051465A, to the plants, or plant parts, of canola DN051465A and to methods for producing a canola plant produced by crossing the canola DN051465A with itself or another canola cultivar, and the creation of variants by mutagenesis or transformation of canola DN051465A.

Thus, any such methods using the canola DN051465A are part of this invention: selfing, backcrossing, hybrid production, crossing to populations, and the like. All plants produced using canola DN051465A as a parent, are within the scope of this invention. Advantageously, the canola DN051465A could be used in crosses with other, different, canola plants to produce first generation ($F_1$) canola hybrid seeds and plants with superior characteristics.

In another aspect, the present invention provides for single or multiple gene-converted plants of canola DN051465A. The transferred gene(s) may preferably have dominant or recessive allele(s). Preferably, the transferred gene(s) will confer such traits as herbicide resistance, insect resistance; resistance to bacterial, fungal, or viral disease; male fertility, male sterility, enhanced nutritional quality, or industrial usage. The gene may be a naturally occurring canola gene or a transgene introduced through genetic engineering techniques.

In another aspect, the present invention provides regenerable cells for use in tissue culture of canola DN051465A. The tissue culture will preferably be capable of regenerating plants having the physiological and morphological characteristics of the foregoing canola plant, and of regenerating plants having substantially the same genotype as the foregoing canola plant. Preferably, the regenerable cells in such tissue cultures will be embryos, protoplasts, meristematic cells, callus, pollen, leaves, anthers, roots, root tips, flowers, seeds, pods or stems. Still further, the present invention provides canola plants regenerated from the tissue cultures of the invention.

In another aspect, the present invention provides a method of introducing a desired trait into canola DN051465A wherein the method comprises: crossing a DN051465A plant with a plant of a different canola genotype that comprises a desired trait to produce $F_1$ progeny plants, wherein the desired trait is selected from the group consisting of male sterility, herbicide resistance, insect resistance, and resistance to bacterial disease, fungal disease or viral disease; selecting one or more progeny plants that have the desired trait to produce selected progeny plants; crossing the selected progeny plants with the DN051465A plants to produce backcross progeny plants; selecting for backcross progeny plants that have the desired trait and physiological and morphological characteristics of canola DN051465A to produce selected backcross progeny plants; and repeating these steps to produce selected first or higher backcross progeny plants that comprise the desired trait and all of the physiological and morphological characteristics of canola DN051465A. Included in this aspect of the invention is the plant produced by the method wherein the plant has the desired trait and all of the physiological and morphological characteristics of canola DN051465A.

In addition to the exemplary aspects and embodiments described above, further aspects and embodiments will become apparent by study of the following descriptions.

DETAILED DESCRIPTION OF THE INVENTION

In the description and examples that follow, a number of terms are used. To provide a clear and consistent understanding of the specification and claims, including the scope to be given such terms, the following definitions are provided.

DEFINITIONS OF PLANT CHARACTERISTICS

Acid Detergent Fiber (ADF): The cell wall portions of the plant material that are made up of cellulose and lignin; measured as a percentage of dry matter. The value, measured by Near Infrared (NIR) Spectroscopy or wet chemistry methods, reflects the ability of an animal to digest the plant material, where the higher the value, the lower the digestibility.

Allele: Any of one or more alternative forms of a gene, all of which relate to the same protein, trait, or characteristic. In a diploid cell or organism, the alleles of a given gene occupy the corresponding locus on a pair of homologous chromosomes.

Anther Arrangement: The orientation of the anthers in fully opened flowers rated as introse (facing inward toward pistil), erect (neither inward not outward), or extrose (facing outward away from pistil).

Anther Dotting: The presence or absence of colored spots on the tips of anthers and if present, the percentage of anthers with dotting in newly opened flowers.

Anther Fertility: The amount of pollen produced on the anthers of a flower; rated as sterile (such as in female parents used for hybrid seed production) to fertile (all anthers shedding).

AOM hours: A measure of the oxidative stability of an oil using currently accepted Official Methods of the American Oil Chemists' Society (eg, AOCS 12b 92).

Backcrossing: A process in which a breeder repeatedly crosses hybrid progeny back to one of the parents; for example, a first generation hybrid F1 crossed back to one of the parental genotypes of the F1 hybrid.

Blackleg Resistance: Resistance of a plant to two fungi (*Leptosphaeria maculans* and *Leptosphaeria biglobosa*) that cause a disease commonly called blackleg; visually rated relative to a highly susceptible check such as the cultivar 'Westar' as Resistant (<30% of Westar), Moderately Resistant (30% to 49% of Westar), Moderately Susceptible (50% to 69% of Westar), Susceptible (70% to 100% of Westar), or Highly Susceptible (>100% of Westar).

Chlorophyll Content: The chlorophyll content of grain; measured using near-infrared (NIR) spectroscopy or other methods recommended by the Western Canada Canola/Rapeseed Recommending Committee (WCC/RRC); rated as milligrams of chlorophyll per kilograms of grain or as low (<8 ppm), medium (8 to 15 ppm), and high (>15 ppm).

Cotyledon Width: The maximum width of a fully developed cotyledon (first photosynthetic leaves) measured around 2 to 3 weeks after emergence when the plant is at the 2-leaf to 3-leaf stage of development and is rated as narrow, medium, or wide.

Cultivar: A plant genotype that has been intentionally bred or selected to be genetically distinct, uniform, and stable, and is maintained through cultivation or other propagation.

Cytoplasmic Male Sterility (CMS): A system by which a plant is unable to produce functional pollen as a result of a genetic abnormality at a locus in its mitochondrial genome. Male fertility may be restored when this male-sterile cytoplasm is combined by crossing to a genotype with a particular complementary allele at a locus in the nuclear genome that suppresses this cytoplasmic dysfunction.

Days to Flowering: The number of days from planting to the stage when 50% of the plants show one or more open flowers.

Days to Maturity: The maturity of a variety measured as the number of days between planting and physiological maturity, i.e., the date when pods ⅓rd up the main raceme have 60% of the seeds expressing a color change from green to brown or black.

Doubled Haploid (Dihaploid): A genotype formed when haploid cells undergo chromosome doubling. Used in plant breeding to develop completely homozygous lines faster than can be done by multiple generations of inbreeding.

Early-Season Vigor (ESV): Assessed at the 4- to 5-leaf stage taking into account plant stand (or emergence) and ground cover of the desired crop; rated on a 1 to 9 scale where 1 is weak vigor and 9 is strong vigor.

Eicosenoic Acid: The total of eicosenoic acid (C20:1) in an oil sample obtained from unprocessed seed; measured as a percentage of total oil.

Elite canola: A canola cultivar that has been stabilized for certain commercially important agronomic traits wherein the relative value of a trait is about 100% or greater relative to the check cultivars growing in the same field location at the same time and under the same conditions. In one embodiment, "elite canola" means a canola cultivar stabilized for yield of 110% or greater relative to the yield of check cultivars growing in the same field location at the same time and under the same conditions. In another embodiment, "elite canola" means a canola cultivar stabilized for yield of 115% or greater relative to the yield of check cultivars growing in the same field location at the same time and under the same conditions.

Embryo: The genetic precursor tissue to the plant contained within and germinating from a mature seed.

Erucic Acid: The total erucic acid (C22:1) in an oil sample obtained from unprocessed seed; measured as a percentage of total oil.

FAME analysis: Quantification of fatty acid methyl esters (FAME) resulting from methylation to separate individual fatty acids from the glycerol backbone in triglycerides.

Fatty Acids: Various sizes of saturated and unsaturated hydrocarbon chains that are found in oil; of which individual sizes can be measured using gas chromatography or Near Infrared Resonance (NIR) spectroscopy as percentages of the total oil extracted from unprocessed seed.

Fertility Restoration: A system by which a dominant fertility-restoration allele (Rf) at a locus in the nuclear genome restores male fertility to a hybrid progeny plant resulting from a cross of this allele to a parent having a compatible cytoplasmic male-sterility (CMS) system.

Flower Bud Location: The location of unopened flower buds relative to adjacent opened flowers rated as above or below the opened flower. The unopened buds are positioned above the most recently opened flowers in *Brassica napus* and positioned below the most recently opened flower buds in *Brassica rapa*.

*Fusarium*-Wilt Resistance: Resistance to two soil-borne fungi (*Fusarium avenaceum* and *Fusarium oxysporum*) that cause a disease commonly called *Fusarium* wilt; visually rated relative to a highly susceptible check as Resistant (<30% of check), Moderately Resistant (30% to 49% of check), Moderately Susceptible (50% to 69% of check), Susceptible (70% to 100% of check), or Highly Susceptible (>100% of check).

Genotype: Refers to either the complete genetic composition or a specific portion of the genetic composition of an organism.

Glucosinolate Content: The total aliphatic glucosinolates expressed as micromoles per gram of whole seed. Glucosinolates can be measured by reversed-phase high-performance liquid chromatography (HPLC) (AOCS Official Method Ak 1-92), by capillary gas chromatography of the trimethylsityl derivatives of extracted and purified desulfo-glucosinolates (Procedures of the Western Canada Canola/Rapeseed Recommending Committee), or by near-infrared (NIR) spectroscopy (AOCS Official Method Am 1-92).

Glyphosate Herbicide Resistance: Resistance of a plant to the action of glyphosate; conferred in crops by genetic transformation of the crop plant using a 5-enol-pyruvylshikimate-3-phosphate synthase (EPSPS) gene that is insensitive to the effect of glyphosate, or a bacterial glyphosate oxidoreductase (GOX) gene that cleaves the nitrogen-carbon bond in glyphosate yielding aminomethylphosphonic acid.

Grain Oil: The oil content, as a percentage of total weight on a dry-matter basis, of whole dried seed.

Grain Protein: The protein content, as a percentage of total weight on a dry-matter basis, of whole dried seed.

Herbicide Resistance: When a plant has negligible effect from contact with an herbicide because the plant does not take up the herbicide or sequesters the herbicide in a manner that renders it harmless.

Herbicide Tolerance: When a plant has negligible effect from contact with an herbicide because the plant metabolically detoxifies the herbicide.

Hybrid: A cultivar or plant-breeding progeny based upon the controlled cross-pollination between or among distinct parent lines, so that the resulting seed inherits its genetic composition from those parent lines. Seed for a particular hybrid can be repeatedly and predictably produced when repeatedly making controlled cross-pollinations from the same stable female and male parent genotypes.

Imidazolinone (Imi) Tolerance: Tolerance of a plant to the action of imidazolinone; conferred by one or more genes that alter acetolactate synthase (ALS), also known as acetohydroxy acid synthase (AHAS), to be insensitive to imidazolinone thereby preventing injury when exposed to this class of herbicides.

Inbred: A relatively stable plant genotype resulting from doubled haploids, successive generations of controlled self-pollination, successive generations of conrolled backcrossing to a recurrent parent, or other method to develop homozygosity.

Leaf Attachment to Stem: The degree to which the base of the leaf blade of the supper stem leaf clasps the stem rated as complete clasping (*Brassica rapa*), partial clasping (*Brassica napus*), or non-clasping (mustard species).

Leaf Color: Leaf blade color recorded at the 5-leaf stage and rated as light green, medium green, dark green, or blue green.

Leaf Glaucosity: Leaf waxiness determined by rubbing the leaf surface; rated as absent or present and, if present, as very weak, weak, medium, strong, or very strong.

Leaf Length: The length of the leaf from the tip to the base of the petiole;
visually determined to be short, medium, or long.

Leaf Lobe: A leaf lobe exists when the leaf tissue is indented in two places to at least half the distance to the midrib. The upper area of the leaf is counted as a lobe (terminal lobe).

Leaf Lobe Development: Lobe development on a fully developed upper-stem leaf before flowering when at least 6 leaves of the plant are completely developed; visually rated as absent or present and, if present, as very weak, weak, medium, strong, or very strong.

Leaf Lobe Number: Count of the leaf lobes on a fully developed upper-stem leaf before flowering when at least 6 leaves of the plant are completely developed.

Leaf Lobe Shape: Shape of the leaf lobes; visually determined to be acute or rounded.

Leaf Margin Indentation: The serration along the margin of a fully developed upper stem leaf measured before flowering when at least 6 leaves of the plant are completely developed; rated as absent or present and, if present, as very weak, weak, medium, strong, or very strong.

Leaf Margin Shape: Shape of the leaf margin on the upper third of the largest leaf; visually determined to be undulating, rounded, or sharp.

Leaf Pubescence: Degree of hairiness on a leaf surface; rated as glabrous (smooth/not hairy, *Brassica napus*) or pubescent (hairy, *Brassica rapa*).

Leaf Shape: Shape of the leaf; visually determined as narrow elliptic (width/length <0.67), wide elliptic (width/length=0.67 to 0.79), or orbicular (width/length >0.79).

Leaf Surface Texture: Degree of leaf-surface wrinkling when at least 6 leaves of the plant are completed developed; rated as smooth or rough.

Leaf Texture: A description of the texture of the leaf surface; visually determined to be smooth or rough.

Leaf Type: Leaf visually rated as petiolate or lyrate.

Leaf Waxiness: A description of the waxiness on the surface of the leaf; visually determined to be absent, weak, medium, strong, or very strong.

Leaf Width: The width of the leaf between its widest points on both edges on opposite sides of the midrib; visually determined to be narrow, medium, or wide.

Linoleic Acid: The total linoleic acid (C18:2) in an oil sample obtained from unprocessed seed; measured as a percentage of total oil.

Linolenic Acid: The total linolenic acid (C18:3) in an oil sample obtained from unprocessed seed; measured as a percentage of total oil.

Lodging Resistance: A scale for the physical orientation of plants after exposure to adverse environmental conditions; generally measured by observing the angle of the stem to the ground on a 1 to 9 scale where 1=flat and 9=fully erect.

Lyrate Leaf: Leaf with laminar tissue continuing along the whole length of the petiole to the auricles.

Maintainer: A sister line of a restorer line and is genetically identical except that it possesses normal cytoplasm and is therefore male-fertile.

Meal Protein: The protein content, as a percentage of total weight on a dry-matter basis, of oil-free meal.

Near Infrared (NIR) Spectroscopy: A spectroscopic method that uses the near-infrared region of the electromagnetic spectrum (from about 800 nm to 2500 nm).

Oil Content: The amount of oil in unprocessed grain as a percentage of the whole dried seed; determined by pulsed nuclear magnetic resonance (NMR) (AOCS Official Method Ak 4-95) or near-infrared (NIR) spectroscopy (AOCS Official Method Am 1-92).

Oleic Acid: The total oleic acid (C18:1) in an oil sample obtained from unprocessed seed; measured as a percentage of total oil.

Palmitic Acid: The total palmitic acid (C16:0) in an oil sample obtained from unprocessed seed; measured as a percentage of total oil.

Petal Color: Flower petal color on open exposed petals; rated the first day of flowering as white, light yellow, medium yellow, dark yellow, orange, or other.

Petal Length: Length of petals; visually determined to be short, medium, or long.

Petal Width: Width of petals; visually determined to be narrow, medium, or wide.

Petal Spacing: The proximity of petals to each other on a fully opened flower; visually determined to be open (large space between petals), not touching (small space between petals), touching, slight overlap, or strong overlap.

Petiolate Leaf: Leaf with a distinct and mostly naked petiole; some discrete petiolar bracts may be present.

Petiole Length: Length of the petiole between where it is attached to the stem and where, at the highest point on the leaf, leaf tissue either joins the midrib or is within 4 mm of the midrib; visually determined to be short, medium, or long.

Plant Growth Habit: The angle of the outermost fully-expanded leaf petioles relative to the soil surface measured at end of flowering; rated as erect (>85°), semi-erect (approximately 65°), semi-prostrate (approximately 45°), or prostrate (<30°).

Plant Height: The height of a plant at the end of flowering from the ground to the top of floral branches that are extended upright (ie, not lodged); visually determined to be short, medium, or tall.

Pod (silique) Angle: The orientation of the pods along the racemes (flowering stems); visually determined to be erect (pods angled close to racemes), semi-erect (pods perpendicular to racemes), slightly drooping (pods show distinct arching habit), or drooping (pods show distinct pointing towards the ground).

Pod (silique) Beak Length: The length of the segment at the end of the pod that does not contain seed (it is a remnant of the stigma and style for the flower); visually determined to be short, medium, or long.

Pod (silique) Length: The length of a fully developed pod; visually determined to be short, medium, or long.

Pod (silique) Pedicel Length: The length of the pedicel, ie, the stem that attaches the pod to the raceme of flowering shoot; visually determined to be short, medium, or long.

Pod (silique) Width: The width of a fully developed pod; visually determined to be narrow, medium, or wide.

Protein Content: The total protein as a percentage by weight of the whole seed or oil-free meal from mature dried grain; determined by a combustion method (AOCS Official Method Ba 4e-93) or near-infrared (NIR) spectroscopy (AOCS Official Method Am 1-92).

Restorer Line: A line possessing the gene or genes to restore male fertility or viable pollen to a sunflower hybrid or inbred line and progeny having a maternal cytoplasm that conditions male sterility.

Saturated Fatty Acids: The total of the saturated fatty acids including C12:0, C14:0, C16:0, C18:0, C20:0, C22:0 and C24:0 as a percentage of the oil from unprocessed seed.

Season Type: The growth habit type of canola rated as spring or winter.

Seed Coat Color: The color of the seed coat of a mature seed rated as black, brown, yellow, mixed, or mottled.

Seed Coat Mucilage: The presence or absence of mucilage in the seed coat;
 detected by imbibing seeds with water and monitoring for mucilage that if present, appears as a halo around the seed. Mucilage is present in the seed coats of *Brassica rapa* and absent in the seed coats of *Brassica napus*.

Seed Weight: The weight in grams of 1000 seeds at maturity at 5% to 6% moisture.

Seedling Growth Habit: The growth habit of the leaf rosette on young seedlings, ie, the first 2 to 8 true leaves; rated before flowering as weak (loosely arranged) or strong (closely packed leaves).

Shatter Resistance: The relative amount of plants within a cultivar that do not drop seed at maturity; rated as not tested, poor, fair, or good.

Single Gene Converted (Conversion): A cultivar developed by backcrossing or inserting into it by genetic transformation, a single gene or tightly linked genes, wherein essentially the remainder of the genome is unchanged.

Species: Whether the claimed canola cultivar is a member of the species *Brassica napus* (tetraploid, AACC genomes), *Brassica rapa* (diploid, AA genome) or *Brassica juncea* (tetraploid, AABB genomes).

Stabilized: Reproducibly passed trait from one generation to the next generation of inbred plants of the same cultivar.

Stearic Acid: The total stearic acid (C18:0) in an oil sample obtained from unprocessed seed; measured as a percentage of total oil.

Stem Anthocyanin: The expression of anthocyanin (a purple pigment) in the stem of plants measured before flowering at the 9- to 11-leaf stage rated as absent or present and, if present, as very weak, weak, medium, strong, or very strong.

Time to Flowering: The number of days from planting to when 50% of plants of a cultivar show one or more open flowers.

Time to Maturity: The number of days from planting to when all seeds on plants of a cultivar complete filling (about 40% moisture).

White-Rust Resistance: Amount of resistance to white rust (*Albugo candida*) rated as a percent of susceptible checks; Race 7A measured on *Brassica rapa*, Races 2V and 7V measured on *Brassica napus*, and Race 2A measured on *Brassica juncea*.

Winter Hardiness: The relative degree to which plants of a winter-type (fall planted) annual cultivar survives the winter; visually determined to be poor, fair, good, or excellent.

Yield: The quantity of grain produced in kilograms per hectare (kg/ha), grams per plot (g/plot), or bushels per acre (bu/ac).

Description of DN051465A

Canola DN051465A is an elite cytoplasmic male-sterile (Ogura) A-line and maintainer B-line. The B line was developed by crossing between elite B-line parents, inbreeding, testing, and selection based on agronomic performance. The A line was developed from a cross between a cytoplasmic male-sterile (Ogura) plant as the female parent and the elite B line as the male parent followed by four generations of backcrossing to, and selection for, the elite male parent nuclear genotype. The A line of DN051465A is reproduced (maintained) by pollination with the cytoplasmic male-fertile isogenic B line of DN051465A, and both A and B lines have shown uniformity and stability of characteristics over multiple generations. DN051465A has shown good combining ability resulting in the identification of a high yielding hybrid with desirable agronomic characteristics.

The present invention relates to a canola plant that expresses substantially all of the physiological and morphological characteristics of inbred line DN051465A. Any plants produced from inbred line DN051465A are contemplated by the present invention and are, therefore, within the scope of this invention. A description of morphological and other characteristics of inbred line DN051465A is presented in Table 1.

TABLE 1

Morphological and Other Characteristics of Canola *Brassica napus* DN051465A

| Characteristic | Value |
| --- | --- |
| Season Type (Spring, Winter) | Spring |
| Type of Cultivar (Hybrid, Pure Line) | Pure Line |
| Pollination Control System | Female CMS A-line |
| BEFORE FLOWERING | |
| Cotyledon Width (3 = Narrow, 5 = Medium, 7 = Wide) | 3 |
| Stem Anthocyanin Intensity (1 = Absent or Very Weak, 3 = Weak, 5 = Medium, 7 = Strong, 9 = Very Strong) | 5 |
| Leaf Type (1 = Petiolate, 9 = Lyrate) | 1 |
| Leaf Shape (3 = Narrow elliptic, 5 = Wide elliptic, 7 = Orbicular) | 3 |
| Leaf Length (3 = Short, 5 = Medium, 7 = Long) | 5 |
| Leaf Width (3 = Narrow, 5 = Medium, 7 = Wide) | 5 |
| Leaf Color (at 5-leaf stage) (1 = Light Green, 2 = Medium Green, 3 = Dark Green, 4 = Blue-Green) | 3 |
| Leaf Waxiness (1 = Absent or Very Weak, 3 = Weak, 5 = Medium, 7 = Strong, 9 = Very Strong) | 5 |
| Leaf Texture (1 = Smooth, 9 = Rough) | 1 |
| Leaf Lobe Development (1 = Absent or Very Weak, 3 = Weak, 5 = Medium, 7 = Strong, 9 = Very Strong) | 5 |
| Leaf Lobe Number (count) | 6 |
| Leaf Lobe Shape (1 = Acute, 9 = Rounded) | |
| Petiole Length (lobed cultivars only) (3 = Short, 5 = Medium, 7 = Long) | 5 |
| Leaf Margin Shape (1 = Undulating, 2 = Rounded, 3 = Sharp) | 3 |
| Leaf Margin Indentation (observe fully developed upper stem leaves) (1 = Absent or Very Weak (very shallow), 3 = Weak (shallow), 5 = Medium, 7 = Strong (deep), 9 = Very Strong (very deep)) | 3 |
| Leaf Attachment to Stem (1 = Complete Clasping, 2 = Partial Clasping, 3 = Non-Clasping) | 2 |
| AFTER FLOWERING | |
| Time to Flowering (days from planting to 50% of plants showing one or more open flowers) | 52 |
| Plant Height at Maturity (3 = Short, 5 = Medium, 7 = Tall) | 5 |
| Flower-Bud Location (1 = Buds above most recently opened flowers, 9 = Buds below most recently opened flowers) | 1 |
| Petal Color (on first day of flowering) (1 = White, 2 = Light Yellow, 3 = Medium Yellow, 4 = Dark Yellow, 5 = Orange, 6 = Other) | 3 |
| Petal Length (3 = Short, 5 = Medium, 7 = Long) | 5 |
| Petal Width (3 = Narrow, 5 = Medium, 7 = Wide) | 3 |
| Petal Spacing (1 = Open, 3 = Not Touching, 5 = Touching, 7 = Slight Overlap, 9 = Strong Overlap) | 1 |
| Anther Dotting (percentage at opening of flower) (1 = absent, 9 = present (percentage)) | 1 |
| Anther Arrangement (observe fully open flower) (1 = Introrse (facing inward), 2 = Erect, 3 = Extrorse (facing outward)) | 2 |
| Anther Fertility (pollen production) (1 = Sterile, 9 = All Anthers Shedding) | 1 |
| Pod (silique) Length (1 = Short (<7cm), 5 = Medium (7 to 10cm), 9 = Long (>10cm)) | 1 |
| Pod (silique) Width (3 = Narrow (3mm), 5 = Medium (4mm), 7 = Wide (5mm)) | 7 |
| Pod (silique) Angle (1 = Erect, 3 = Semi-Erect, 5 = Horizontal, 7 = Slightly Drooping, 9 = Drooping) | 3 |
| Pod (silique) Beak Length (3 = Short, 5 = Medium, 7 = Long) | 3 |
| Pod Pedicel Length (3 = Short, 5 = Medium, 7 = Long) | 5 |

TABLE 1-continued

Morphological and Other Characteristics of Canola Brassica napus DN051465A

| Characteristic | Value |
| --- | --- |
| REACTION TO CHEMICALS | |
| Herbicides | imidazolinone tolerant |
| QUALITY | |
| Fatty-Acid Composition (percentage of total fatty acids in seed oil) | |
| Oleic Acid (C18:1) | 72.67 |
| Linoleic Acid (C18:2) | 18.56 |
| Linolenic Acid (C18:3) | 1.44 |
| % Oil DM | 48.29 |
| % Protein DM | 26.41 |
| % ADF | 13.5 |

DN051465A has exhibited commercial value in multi-year, multi-location field evaluations. The commercial utility is enhanced by the valuable combination of grain yield; tolerance to imidazolinone herbicides; high oleic, low linolenic, low erucic acid oil profile; high oil; high protein; and low glucosinolates. DN051465A is an elite canola line with grain quality and yield similar or superior to other elite germplasm (Tables 2 and 3).

TABLE 2

Grain Quality of Canola Brassica napus DN051465A Compared to Control Cultivars at 1 Mid-Season-Zone Field Nursery Location, 2011[1]

| Cultivar Name | C18:1 NIR | C18:2 NIR | C18:3 NIR | % Oil DM | % Protein DM | Chlorophyll (mg/kg) | % ADF |
| --- | --- | --- | --- | --- | --- | --- | --- |
| Nex 840 CL, 2 rep mean | 72.40 | 19.14 | 1.58 | 49.10 | 25.43 | 4.00 | 8.10 |
| Nex 845 CL, 6 rep mean | 74.24 | 18.41 | 1.12 | 49.94 | 24.92 | 3.10 | 11.22 |
| DN051465A, 2 rep mean | 72.67 | 18.56 | 1.44 | 48.29 | 26.41 | 14.80 | 13.50 |

[1]Near Pike Lake, Saskatchewan.

TABLE 3

Grain Quality of Canola Brassica napus DN051465A Compared to Control Cultivars at 2 Mid-Season-Zone Trial Locations, 2011[1]

| Cultivar Name | Yield (Kg/Ha) | Vigor of plants in Spring (1-9) 9 = high | Days to Flower | Days to Maturity | Resistance to Lodging (1-9) 9 = high | HGT (cm) |
| --- | --- | --- | --- | --- | --- | --- |
| Nex 840 CL | 2413.4 | 5 | 47.0 | 97.0 | 6 | 93 |
| Nex 845 CL | 2882.0 | 6 | 45.0 | 94.5 | 7 | 90 |
| DN051465A | 2790.4 | 6 | 49.0 | 94.5 | 6 | 105 |

[1]Near Cudworth and Rosthern SK

This invention is also directed to methods for producing a canola plant by crossing a first parent canola plant with a second parent canola plant, wherein the first or second canola plant is a canola plant from DN051465A. Further, both first and second parent canola plants may be from DN051465A. Therefore, any methods using DN051465A are part of this invention: selfing, backcrosses, hybrid breeding, and crosses to populations. Any plants produced using DN051465A as parents are within the scope of this invention.

Useful methods include, but are not limited to, expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-mediated transformation. Transformant plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed inbred line.

Plant transformation involves the construction of an expression vector that will function in plant cells. Such a vector comprises DNA comprising a gene under control of or operatively linked to a regulatory element (for example, a promoter). The expression vector may contain one or more such operably-linked gene/regulatory element combinations. The vector(s) may be in the form of a plasmid, and can be used alone or in combination with other plasmids, to provide transformed canola plants, using transformation methods as described below to incorporate transgenes into the genetic material of the canola plant(s).

Expression Vectors for Canola Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent, which may be an antibiotic or an herbicide, or genes that encode an altered target that is insensitive to the inhibitor. A few positive selection methods are also known in the art.

One commonly used selectable marker gene for plant transformation is the neomycin phosphotransferase II (nptll) gene under the control of plant regulatory signals that confer resistance to kanamycin. Fraley et al., *Proc. Natl. Acad. Sci. U.S.A.*, 80:4803 (1983). Another commonly used selectable marker gene is the hygromycin phosphotransferase gene that confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate, or bromoxynil. Comai et al., *Nature* 317:741-744 (1985); Gordon-Kamm et al., *Plant Cell* 2:603-618 (1990); and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987); Shah et al., *Science* 233:478 (1986); Charest et al., *Plant Cell Rep.* 8:643 (1990).

Another class of marker genes for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987); Teeri et al., *EMBO J.* 8:343 (1989); Koncz et al., *Proc. Natl. Acad. Sci U.S.A.* 84:131 (1987); DeBlock et al., *EMBO J.* 3:1681 (1984).

Recently, in vivo methods for visualizing GUS activity that do not require destruction of plant tissue have been made available. Molecular Probes publication 2908, *Imogene*, Green, T. M., p. 1-4(1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Canola Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissues are referred to as "tissue-specific." A "cell type" specific promoter primarily drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters

An inducible promoter is operably linked to a gene for expression in canola. Optionally, the inducible promoter is operably linked to a nucleotide sequence encoding a signal sequence that is operably linked to a gene for expression in canola. With an inducible promoter, the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system, which responds to copper (Mett et al., *PNAS* 90:4567-4571 (1993)); In2 gene from maize, which responds to benzenesulfonamide herbicide safeners (Hershey et al., *Mol. Gen Genetics* 227:229-237 (1991); and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in canola or the constitutive promoter is operably linked to a nucleotide sequence encoding a signal sequence that is operably linked to a gene for expression in canola.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter is operably linked to a gene for expression in canola. Optionally, the tissue-specific promoter is operably linked to a nucleotide sequence encoding a signal sequence that is operably linked to a gene for expression in canola. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment, or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., A short amino acid sequence able to specify nuclear location, *Cell* 39:499-509 (1984); Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods, which are discussed, for example, by Heney and Orr, *Anal. Biochem.* 114:92-6 (1981).

According to a particular embodiment, the transgenic plant provided for commercial production of foreign protein is a canola plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example, Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); and Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* .alpha.-amylase inhibitor); and U.S. Pat. No. 5,494,813 (Hepher and Atkinson, issued Feb. 27, 1996).

F. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor); and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyperaccumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase; and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones; and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

M. A membrane permease, a channel former or a channel blocker. For example, see the disclosure of Jaynes et al., *Plant Sci.* 89:43 (1993), of heterologous expression of a cecropin-.beta., lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988); and Mild et al., *Theor. Appl. Genet.* 80:449 (1990), respectively.

B. Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (AC-Case inhibitor-encoding genes), See, for example, U.S. Pat. No. 4,940,835 to Shah, et al. and U.S. Pat. No. 6,248,876 to Barry et. al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al., DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Accl-S1, Accl-S2 and Accl-S3 genes described by Marshall et al., *Theor. Appl. Genet.* 83:435 (1992). GAT genes capable of conferring glyphosate resistance are described in WO 2005012515 to Castle et. al. Genes conferring resistance to 2,4-D, fop and pyridyloxy auxin herbicides are described in WO 2005107437 and U.S. patent application Ser. No. 11/587,893, both assigned to Dow AgroSciences LLC.

C. An herbicide that inhibits photosynthesis, such as a triazine (psbA and gs+ genes) or a benzonitrile (nitrilase gene). Przbila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene); Steinmetz et al., *Mol. Gen. Genet.* 20:220 (1985) (nucleotide sequence of *Bacillus subtilis* levansucrase gene); Pen et al., *Bio/Technology* 10:292 (1992) (production of transgenic plants that express *Bacillus lichenifonnis* α-amylase); Elliot et al., *Plant Molec. Biol.* 21:515 (1993) (nucleotide sequences of tomato invertase genes); Sogaard et al., *J. Biol. Chem.* 268:22480 (1993) (site-directed mutagenesis of barley α-amylase gene); and Fisher et al., *Plant Physiol.* 102:1045 (1993) (maize endosperm starch branching enzyme II).

Methods for Canola Transformation

Numerous methods for plant transformation have been developed including biological and physical plant transformation protocols. See, for example, Mild et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. Agrobacterium-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Mild et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Technology* 6:559-563 (1988); Sanford, J. C., *Physiol Plant* 7:206 (1990); Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO. J.*, 4:2731 (1985); Christou et al., *Proc. Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985); and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992); and Spencer et al., *Plant Mol. Biol.* 24:51-61 (1994).

Following transformation of canola target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular canola cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Canolas

Further production of the DN051465A can occur by self-pollination or by tissue culture and regeneration. Tissue culture of various tissues of canola and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," *Plant Cell Reports* 4:4-6 (1985); Barsby, T. L., et al., "A Rapid and Efficient Alternative Procedure for the Regeneration of Plants from Hypocotyl Protoplasts of *Bras-* sica napus," *Plant Cell Reports* (Spring, 1996); Kartha, K., et al., "In vitro Plant Formation from Stem Explants of Rape," *Physiol. Plant*, 31:217-220 (1974); Narasimhulu, S., et al., "Species Specific Shoot Regeneration Response of Cotyledonary Explants of Brassicas," *Plant Cell Reports* (Spring 1988); Swanson, E., "Microspore Culture in *Brassica*," *Methods in Molecular Biology*, Vol. 6, Chapter 17, p. 159 (1990).

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," *Crop Sci.* 31:333-337 (1991); Stephens, P. A., et al., "Agronomic Evaluation of Tissue-Culture-Derived Soybean Plants," *Theor. Appl. Genet.* (1991) 82:633-635; Komatsuda, T. et al., "Maturation and Germination of Somatic Embryos as Affected by Sucrose and Plant Growth Regulators in Soybeans *Glycine gracilis* Skvortz and *Glycine max* (L.) Men." *Plant Cell, Tissue and Organ Culture*, 28:103-113 (1992); Dhir, S. et al., "Regeneration of Fertile Plants from Protoplasts of Soybean (*Glycine max* L. Men.); Genotypic Differences in Culture Response," *Plant Cell Reports* (1992) 11:285-289; Pandey, P. et al., "Plant Regeneration from Leaf and Hypocotyl Explants of Glycine-wightii (W. and A.) VERDC. var. longicauda," *Japan J. Breed.* 42:1-5 (1992); and Shetty, K., et al., "Stimulation of In Vitro Shoot Organogenesis in *Glycine max* (Merrill.) by Allantoin and Amides," *Plant Science* 81:245-251 (1992). The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference. Thus, another aspect of this invention is to provide cells which upon growth and differentiation produce canola plants having the physiological and morphological characteristics of canola DN051465A.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, describe certain techniques, the disclosures of which are incorporated herein by reference.

Single-Gene Converted (Conversion) Plants

When the term "canola plant" is used in the context of the present invention, this also includes any single-gene conversions of that variety. The term "single-gene converted plant" as used herein refers to those canola plants that are developed by a plant breeding technique called backcrossing, or via genetic engineering, wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental canola plant that contributes the gene for the desired characteristic is termed the "nonrecurrent" or "donor parent." This terminology refers to the fact that the nonrecurrent parent is used one time in the backcross protocol and therefore does not recur. The parental canola plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single-gene traits have been identified that are not regularly selected for in the development of a new variety but that can be improved by backcrossing techniques. Single-gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these single-gene traits are described in U.S. Pat. Nos. 5,959,185, 5,973,234 and 5,977,445, the disclosures of which are specifically hereby incorporated by reference.

This invention also is directed to methods for producing a canola plant by crossing a first parent canola plant with a second parent canola plant wherein the first or second parent canola plant is a canola plant of DN051465A. Further, both first and second parent canola plants can come from the canola DN051465A. Thus, any such methods using the canola inbred line DN051465A are part of this invention: selfing, backcrosses, hybrid production, crosses to populations, and the like. All plants produced using canola DN051465A as a parent are within the scope of this invention, including those developed from varieties derived from canola DN051465A. Advantageously, the canola variety could be used in crosses with other, different, canola plants to produce first generation ($F_1$) canola hybrid seeds and plants with superior characteristics. The inbred line of the invention can also be used for transformation where exogenous genes are introduced and expressed by the inbred line of the invention. Genetic variants created either through traditional breeding methods using DN051465A or through transformation of DN051465A by any of a number of protocols known to those of skill in the art are intended to be within the scope of this invention.

The invention is also directed to canola meal from seeds of an elite canola inbred line. In a particular embodiment, the seeds comprise at least 44% protein by weight. Canola meal of the present invention can contain a characteristic selected from the list consisting of low fiber content and high protein compared to presently used canola meal.

Oxidative Stability

Stability can be defined as the resistance of a vegetable oil to oxidation and to the resulting deterioration due to the generation of products causing rancidity and decreasing food quality. Tests for oxidative stability attempt to accelerate the normal oxidation process to yield results that can be translated into quality parameters for different food oils and to predict their shelf lives. Stability methods are also useful to evaluate antioxidants and their effects on protection of foods against lipid oxidation.

Lipid oxidation in food products develops slowly initially, and then accelerates at later stages during storage. The induction period is defined as the time to reach a constant percentage oxidation of the fat as related to the end of shelf life. The induction period is measured either as the time required for a sudden change in rate of oxidation or as the intersection point between the initial and final rates of oxidation. For vegetable oils containing linoleic and linolenic acid, such as soybean and canola oils, the end-points for acceptability will occur at relatively low levels of oxidation (peroxide values between 1 and 10 Meq/kg).

Factors Affecting Oxidative Stability

The difference in stability between different vegetable oils is due to their different fatty acid profiles, the effect of processing, initial levels of oxidation at the start of the storage period, and other factors including, minor components, including the presence of metal impurities, formulation, packaging and environmental storage conditions. From the crude stage to different stages of processing of vegetable oils, some oxidation can take place that will affect the subsequent oxidative stability of the final oil product during storage.

Oxidative Stability Methods

To estimate the oxidative stability of a fat to oxidation, the sample is subjected to an accelerated oxidation test under standardized conditions and a suitable end-point is chosen to determine the level of oxidative deterioration. Methods involving elevated temperatures include:

1. Schaal Oven Test

The sample is heated at 50 to 60° C. until it reaches a suitable end-point based on peroxide value or carbonyl value such as the anisidine value. The results of this test correlate best with actual shelf life because the peroxide value end-point of 10 represents a relatively low degree of oxidation. See, limiting peroxide value in section D below.

2. Active Oxygen Method (AOM), Rancimat and Oxidation Stability Index (OSI). See, e.g., U.S. Pat. No. 5,339,294 to Matlock et. al., *AOCS Method* 12b-92; and Laubli, M. W. and Bruttel, P. A., *JOACS* 63:792-795 (1986).

Air is bubbled through a sample of oil in special test tubes heated at 98-100° C. and the progress of oxidation is followed by peroxide value determination in the AOM test, and by conductivity measurements in the Rancimat and OSI tests. The automated Rancimat and OSI tests may be run at temperatures ranging from 100-140° C., and the effluent gases are led through a vessel containing deionized water and the increase in conductivity measured are due to the formation of volatile organic acids (mainly formic acid) by thermal oxidation. The OSI is defined as the time point in hours of maximum change of the rate of oxidation based on conductivity.

D. Methods to Determine Oxidation—The peroxide value of oils is a measure of oxidation that is useful for samples that are oxidized to relatively low levels (peroxide values of less than 50), and under conditions sufficiently mild so that the hydroperoxides, which are the primary products formed by oxidation, are not markedly decomposed. A limiting peroxide value of 10 meq/kg was specified for refined oils by FAQ/WHO standards (Joint FAQ/WHO Food Standard Program Codex *Alimentarius* Commission, Report of 16th session of Committee on Fats and Oils, London, 1999).

The anisidine test measures high molecular weight saturated and unsaturated carbonyl compounds in oils. The test provides useful information on non-volatile carbonyl compounds formed in oils during processing of oils containing linolenate (soybean and rapeseed). The Totox value (anisidine value+2 times peroxide value) is used as an empirical measure of the precursor non-volatile carbonyl compounds present in processed oils plus any further oxidation products developed after storage.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions and sub-combinations as are within their true spirit and scope.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

DEPOSIT INFORMATION

A deposit of the Dow AgroSciences proprietary canola DN051465A disclosed above and recited in the appended claims has been made with the American Type Culture Collection (ATCC), 10801 University Boulevard, Manassas, Va. 20110. The date of deposit was Jan. 11, 2015. The deposit of 2500 seeds were taken from the same deposit maintained by Agrigenetics, Inc. since prior to the filing date of this application. All restrictions upon the deposit have been removed, and the deposit is intended to meet all of the requirements of 37 C.F.R. Sections 1.801-1.809. The ATCC accession number is PTA-122824. The deposit will be maintained in the depository for a period of 30 years, or 5 years after the last request, or for the effective life of the patent, whichever is longer, and will be replaced as necessary during that period.

What is claimed is:

1. A seed of canola designated DN051465A, wherein a representative sample of seed of said cultivar was deposited under ATCC Accession No. PTA-122824.

2. A canola plant, or a part thereof, produced by growing the seed of claim 1.

3. A method of introducing a desired trait into canola DN051465A, wherein the method comprises: (a) crossing a DN051465A plant, wherein a representative sample of seed was deposited under ATCC Accession No. PTA-122824, with a second plant of another canola cultivar that comprises a desired trait to produce $F_1$ progeny plants, wherein the desired trait is selected from the group consisting of herbicide resistance, insect resistance, and resistance to bacterial disease, fungal disease or viral disease; (b) selecting one or more progeny plants that have the desired trait to produce selected progeny plants; (c) crossing the selected progeny plants with the DN051465A plants to produce backcross progeny plants; (d) selecting for backcross progeny plants that have the desired trait and physiological and morphological characteristics of canola DN051465A to produce selected backcross progeny plants; and (e) repeating steps (c) and (d) three or more times to produce selected fourth or higher backcross progeny plants that comprise the desired trait and an oleic acid value of about 70% and an α-linolenic acid value of less than about 3% as a percentage of total fatty acids, comprise all of the physiological and morphological characteristics of canola DN051465A, and further comprise the desired trait.

4. The method of claim 3, wherein the selected fourth or higher backcross progeny plants further comprise a yield greater than about 2100 kg/ha, a protein value of greater than 44%, or a glucosinolate value of less than 12%, as measured as a percentage by weight of oil-free meal.

5. The method of claim 3, wherein the resistance to bacterial disease, fungal disease or viral disease is selected from the group consisting of Blackleg (*Leptosphaeria maculans*), *Fusarium* wilt, or White Rust resistance.

6. The method of claim 3, wherein resistance to an herbicide is selected from the group consisting of imidazolinone, sulfonylurea, glyphosate, glufosinate, L-phosphinothricin, triazine, Clearfield, Dicamaba, 2,4-D, and benzonitrile.

7. The method of claim 3, wherein the selected fourth or higher backcross progeny plants comprise all of the physiological and morphological characteristics of canola DN051465A as shown in Tables 1, 2 and 3.

8. A selected fourth or higher backcross progeny canola plant produced by the method of claim 3, wherein the selected fourth or higher backcross progeny plant has the desired trait and comprises an oleic acid value of about 70% and an α-linolenic acid value of less than about 3% as a percentage of total fatty acids.

9. The canola plant of claim 8, wherein the herbicide resistance is conferred to an herbicide selected from the group consisting of imidazolinone, sulfonylurea, glyphosate, glufosinate, L-phosphinothricin, triazine, Clearfield, Dicamaba, 2,4-D, and benzonitrile.

10. The selected fourth or higher backcross progeny canola plant of claim 8, wherein the insect resistance is conferred by a transgene encoding a *Bacillus thuringiensis* endotoxin.

11. The selected fourth or higher backcross progeny canola plant of claim 8, wherein the resistance to bacterial disease, fungal disease or viral disease is selected from the group consisting of Blackleg, *Fusarium* wilt, or White Rust resistance.

12. The selected fourth or higher backcross progeny canola plant of claim 8, wherein the plant comprises all of the physiological and morphological characteristics of canola DN051465A, as shown in Tables 1, 2, and 3.

13. A method of modifying fatty acid metabolism or modifying carbohydrate metabolism of canola DN051465A wherein the method comprises: (a) crossing a DN051465A plant, wherein a representative sample of seed was deposited under ATCC Accession No. PTA-122824, with a plant of another canola cultivar to produce $F_1$ progeny plants that comprise a nucleic acid molecule encoding an enzyme selected from the group consisting of phytase, fructosyltransferase, levansucrase, alpha-amylase, invertase and starch branching enzyme or encoding an antisense of stearyl-ACP desaturase; (b) selecting one or more progeny plants that have said nucleic acid molecule to produce selected progeny plants; (c) crossing the selected progeny plants with the DN051465A plants to produce backcross progeny plants; (d) selecting for backcross progeny plants that have said nucleic acid molecule and physiological and morphological characteristics of canola DN051465A to produce selected backcross progeny plants; and (e) repeating steps (c) and (d) three or more times to produce selected fourth or higher backcross progeny plants that comprise said nucleic acid molecule and have an oleic acid value of about 70% and an α-linolenic acid value of less than about 3% as a percentage of total fatty acids, comprise all of the physiological and morphological characteristics of canola DN051465A, and further comprise the desired trait.

14. The method of claim 13, wherein the selected fourth or higher backcross progeny plants further comprise a yield greater than about 2100 kg/ha, a protein value of greater than 44%, or a glucosinolate value of less than 12% as measured as a percentage by weight of oil-free meal.

15. The method of claim 13, wherein the resistance to bacterial disease, fungal disease or viral disease is selected from the group consisting of Blackleg (*Leptosphaeria maculans*), *Fusarium* wilt, or White Rust resistance.

16. The method of claim 13, wherein resistance to an herbicide is selected from the group consisting of imidazolinone, sulfonylurea, glyphosate, glufosinate, L-phosphinothricin, triazine, Clearfield, Dicamaba, 2,4-D, and benzonitrile.

17. The method of claim 13, wherein the selected fourth or higher backcross progeny plants comprise all of the physiological and morphological characteristics of canola DN051465A as shown in Tables 1, 2 and 3.

18. A selected fourth or higher backcross progeny canola plant produced by the method of claim 13, wherein the selected fourth or higher backcross progeny plant comprises the nucleic acid molecule and has an oleic acid value of about 70% and an α-linolenic acid value of less than about 3% as a percentage of total fatty acids.

19. A selected fourth or higher backcross progeny canola plant produced by the method of claim 13, wherein the plants further comprise a yield greater than about 2100 kg/ha, a protein value of greater than 44%, or a glucosinolate value of less than 12% as measured as a percentage by weight of oil-free meal.

20. A selected fourth or higher backcross progeny canola plant produced by the method of claim 13, wherein the plants comprise all of the physiological and morphological characteristics of canola DN051465A as shown in Tables 1, 2 and 3.

* * * * *